United States Patent [19]
Beltzer et al.

[11] 3,986,386
[45] Oct. 19, 1976

[54] PARTICULATE SAMPLING SYSTEM

[75] Inventors: Morton Beltzer, Westfield; William L. Petersen, Dunellen; Oliver G. Lewis, Westfield; George S. Musser, Warren, all of N.J.

[73] Assignee: Exxon Research and Engineering Company, Linden, N.J.

[22] Filed: Apr. 12, 1974

[21] Appl. No.: 460,291

[52] U.S. Cl. .............................. 73/28; 73/421.5 R
[51] Int. Cl.² .......................................... G01N 1/22
[58] Field of Search.......... 73/28, 421.5 R, 421.5 A; 62/186

[56] References Cited
UNITED STATES PATENTS

| 2,819,590 | 1/1958 | Green | 62/186 X |
|---|---|---|---|
| 3,102,192 | 8/1963 | Skala | 73/28 X |
| 3,261,199 | 7/1966 | Raynor | 73/421.5 R X |
| 3,391,577 | 7/1968 | Friauf et al. | 73/421.5 R |
| 3,611,812 | 10/1971 | Cleveland | 73/421.5 R |
| 3,866,475 | 2/1975 | Thompson et al. | 73/421.5 R |

*Primary Examiner*—Charles E. Phillips
*Attorney, Agent, or Firm*—H. N. Wells; R. D. Hantman

[57] ABSTRACT

A method and apparatus for measuring particulates contained in the exhaust gases from internal combustion engines which dilutes the exhaust gases with prefiltered and precooled air to produce a constant volume mixture which may be sampled for exhaust gas emissions as well as for particulates. After mixing of the exhaust gases and the pretreated air, sampling of the mixture by isokinetic probes produces a uniform sample of particulate matter which is collected on temperature controlled filters for analysis.

13 Claims, 5 Drawing Figures

PARTICULATE SAMPLING SYSTEM

BACKGROUND OF THE INVENTION

Measurement of automotive exhaust gases for hydrocarbons, CO, and $NO_x$ has been common in recent years as Federal standards of increasing severity have been applied. measurement of particulates in exhaust emissions has been of interest, although no standards for these emissions have been established. Automotive particulate emissions in general may be defined as any material, other than unbound water, which condenses at 90°F. into particles larger than a small molecule, but smaller than 500 microns in diameter. Concerns over these emissions are related to the potential effects on human health which may result from the formation of these minute particles in the atmosphere. Such particles could among other things possibly function as sites for condensed phase chemical reactions to assist in the production of smog. Larger particles, notably lead particles, produced from atomotive exhaust settle rapidly and do not remain suspended for long periods as do the smaller particles toward which the present invention is directed. Earlier investigations were particularly concerned with the production of lead compounds resulting from the use of tetraethyl lead in motor gasoline. More recently, particulate emissions from automobiles operating with catalylic converters which are likely to be required to meet Federal standards have been of concern.

Typical of earlier work was that reported by J. B. Moran and O. J. Manary, Interim Report PB196783, "Effect of Fuel Additives on the Chemical and Physical Characteristics of Particle Emissions in Automotive Exhausts", NAPCA, July, 1970, and K. Habibi, "Automotive Particulate Emissions and their Control", SAE Paper 710638, Oct. 24, 1970, Midland, Michigan. This earlier work was primarily related to lead compounds and used equipment which is not suitable for measuring the smaller particles of present concern, especially where these particles must be collected over a rather short test period with the extremely irregular operation of the vehicle typical of a programmed trip cycle. Accordingly, there has been a need for measurement of the small particulates in a manner which would give rapid and reproducible results suitable for use with the standard Federal test cycles. The present invention is a method and apparatus which accomplishes this objective.

Making such measurements is a more difficult task than might be at first thought. In a typical test cycle, the automobile exhaust gases may range from 20 standard cubic feet per minute up to 200 standard cubic feet per minute, constantly changing as the vehicle accelerates or deaccelerates according to the standard program. In order to insure uniformity of results, it is desired to maintain a constant temperature filtration of the exhaust, which is incompatible with the marked variations in flow rate which are typical of a test cycle. This temperature has been selected on a preliminary basis to be 90°F., which introduces the possibility that condensation of water in the exhaust will occur, thus scrubbing a portion of the particulate matter from the exhaust. Since only small quantities of particulates are produced during a typical cycle of perhaps 20 to 40 minutes, it is essential that all of these particles be caught and retained in the filter in order to give accurate and repeatable results. It is neither practical nor possible to adopt the technique of some of the earlier investigators, which involved disassembling the apparatus and cleaning it internally in order to recover the last traces of particles which have been produced. Since repetitive tests are run, it is important that equipment not require disassembly and that all of the particles produced be trapped by the filter for analysis. What is required then is that particles leaving the tailpipe of an automobile or other vehicle must be thoroughly mixed with dilution air, which will be discussed more fully later, and the particles must not be lost between the mixing point and the filter assembly, either due to settling or wall impactions. It will be clear that some residence time is necessary to provide suitable mixing and in any case is unavoidable in construction of the apparatus. In addition, the system cannot operate at such a temperature that condensation of water from the exhaust will occur. If it does, the scrubbing action produced will remove particulate matter, giving irregular and obviously erroneous results. Also, particle agglomeration would be likely to occur during the condensation process, making measurement of the distribution of particulate matter impossible. Only a portion of the total exhaust is actually filtered, making the mixing process particularly significant if the sample is to correctly reflect the composition of the exhaust gas. Another problem not immediately evident is that since cooling to approximately 90°F. is required, this cooling must be done in such a manner that thermophoretic deposition will not occur. Once the exhaust gases have been cooled and mixed, a uniform and reproducible sample must be taken in order to determine the quantity, chemical composition, and size of the particles. Isokinetic sampling which is known broadly in the solids sampling art is utilized in the present invention. However, inasmuch as the quantity of particulate matter is small and the time over which it is collected is relatively short, the isokinetic sampling system itself is subject to some of the problems which have already been discussed with regard to particulate losses. Accordingly, the isokinetic sampling system itself must prevent particulate losses. The particulate sampling system should be compatible with the constant volume sampling system which is used in the measurement of other exhaust gaseous emissions; that is, both gaseous and particulate emissions should be measured at the same time over any typical test cycle simultaneously. This constant volume sampling system has been referred to earlier in connection with the dilution of exhaust gas with air. Since a vehicle during a typical test cycle will produce a wide variation in exhaust gas flow rates, and presumably in compositions as well, it is necessary to sample the exhaust gases at varying rates corresponding to their production. The constant volume sampling procedure provides for dilution of the exhaust gases with an amount of air which is sufficient to produce a constant total volume of exhaust gas and air. Once a constant volume is obtained, then sampling can be done at a constant rate no matter what exhaust gas rate is being produced and if the exhaust gases and air are completely mixed, the sample will be proportional to the amount of exhaust gas being produced at any given time in the test cycle. It will be appreciated that the constant volume system could be useful for particulate sampling as well. The introduction of air is beneficial to particulate sampling in that condensation of exhaust gases can be partially prevented. However, it is not eliminated; it has been found that at points in a typical test cycle the 90°F. temperature which is desirable for filtering particles will result in condensation of exhaust gases even though diluted by ambient air. Of course, on extremely humid days the problem will be more severe than in dry weather. Temperature of ambient air also varies widely so that a complicating factor is introduced into the particulate sampling since a constant temperature must always be available at the filter, which collects the particulate matter. In view of the difficulties and problems which have been outlined above, it will be appreciated that the accurate sampling of particulate emissions in automotive exhaust represents a difficult problem, but it has been solved by the method and apparatus of the present invention.

SUMMARY OF THE INVENTION

A method and apparatus for measuring particulate emissions from internal combustion engines includes means for conditioning a stream of air and thoroughly mixing it with exhaust gases from the engine to produce a constant total flow rate and temperataure. Once thoroughly mixed and temperature adjusted, the mixture of gas and air is sampled by an isokinetic probe, which avoids significant deposition of particles before the sample stream is passed through a filter which collects essentially all of the particulate matter. Temperature control of the filter is achieved by controlling the temperature of the mixed exhaust gas and air. Since in a typical test cycle the exhaust gas rate will vary widely, the amount of air needed for makeup to the constant volume sampling system will also be varying continually. Continuous adjustment of the degree of cooling of the changing volume of incoming air is possible with the preferred apparatus of the invention. Apparatus according to the invention has been able to meet the requirements for a particulate sampling system giving repeatable results with insignificant losses and it is possible to run repeated tests without disassembly of the appartus.

DESCRIPTION OF THE PREFERRED EMBODIMENTS

Figure 1:
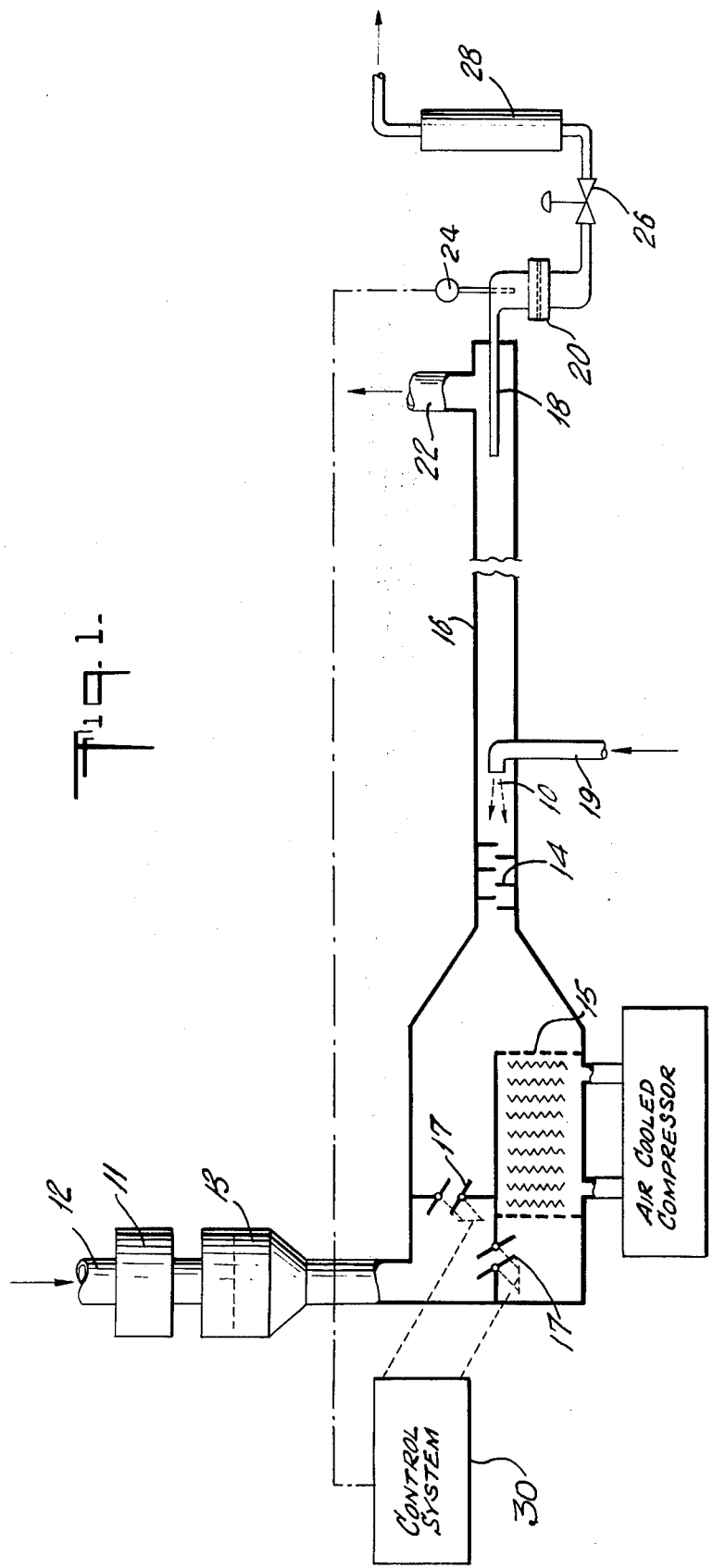
FIG. 1 is a schematic view of an apparatus of the invention.

A schematic illustration of the apparatus according to the invention is shown in FIG. 1. Exhaust from a vehicle undergoing tests will be injected via injector 19 having an inlet nozzle into a stream of air entering at 12 to produce a constant combined volume, even though the amount of exhaust gas varies widely over a typical test cycle. Air and exhaust are passed through a flow development tunnel 16 to assure complete mixing, wherein said mixing means includes the inlet nozzle and the flow development tunnel 16. Isokinetic sampling probe 18 extracts a quantity of gas proportional to the ratio of its open area to the cross sectional area of the flow development tunnel. When sampling a two-phase mixture isokinetic sampling is important to assure that the sample which is taken is truly representative of the bulk. It will be appreciated that if greater or less than the proportional amount were actually sampled, that particles might either preferentially enter the probe or be diverted around it. By not changing the velocity of the sample, the probe does not affect the main stream which is sampled. The sample taken by the isokinetic probe 18 is passed through a filter 20 sized to collect essentially all of the fine particulate matter of 0.2 micron diameter and larger present in a typical internal combustion engine exhaust. The main bulk of the mixture passes via duct 22 to the constant volume sampling system (not shown) which produces the constant volumetric rate in a manner to be discussed later and which also collects a sample for determination of gaseous emissions. Since a constant volumetric rate is always flowing through the tunnel 16, the isokinetic sampling probe 18 must extract a constant volume sample at all times. This is accomplished by means of a vacuum pump (not shown) which is connected to the sampling probe 18 by means of a rotometer 28 and control valve 26 which can be adjusted to produce the desired proportional sample.

The sample is collected at a substantially constant temperature of 90°F. to assure reproducibility of results. Temperature of the sample is measured by thermocouple 24 temperature control means 30 maintains a constant temperature in the filter means 20 by adjusting a cooling means of the incoming air. Even though the typical test cycle will produce a wide variation in exhaust flow rates and temperatures and the dilution air will change also, the temperature of the mixture of exhaust gases and air can be controlled by the apparatus of the invention. The problem will be appreciated by reference to the lower half of FIG. 3, to be discussed later, but which may be inspected at this point to appreciate the wide variation in vehicle speed which is introduced in the standard program cycle established by the Environmental Protection Agency for vehicle certification in 1972. This program cycle lasts approximately 23 minutes and used speeds of up to 58 miles per hour. It will be appreciated that the constant volume sampling system has a difficult job to do in order to introduce a varying quantity of air to combine with the exhaust gases which are produced by this irregular cycle. However, this must be accomplished in order to permit the sampling system to be truly representative of the exhaust emissions. In addition, the temperature adjusting system to be discussed must also respond to these wide variations in air flow.

Turning to the inlet air system of FIG. 1, it will be seen that ambient air is first dehumidified in drier 11, preferably by a solid desiccant which can be regenerated. Commercially available equipment has been adopted for the preferred apparatus of the invention, although other methods of dehumidification might be used. On leaving the drier 11, the humidity of the exiting air is typically 10%, equivalent to a dew point of about 25°F. At least a 30°F. dew point will be required to avoid any possibility of condensation. After moisture removal the incoming air is filtered in filter 13 in order to remove particulates which could disturb the performance of the particulate collection system. Following filtration, the air is cooled to compensate for the hot engine exhaust which is typically 300°F., but which may range between 300° and 800°F., depending on the engine performance. For temperature control, the air is split into two portions by adjustable means 17, the first portion passing through a refrigerated cooler 15 to lower its temperature and the second portion bypassing the cooler 15 so that the required temperature is achieved when the two streams are mixed. The streams are mixed together to produce a uniform temperature by means of mixing baffles 14 located upstream of the exhaust injector 19. After the air has been mixed, exhaust gases are injected at 10 and the exhaust gases and air are completely mixed. It has been found that the preferred method is, as shown here, to introduce the exhaust gases facing into the flow of the dilution air in order to assure proper distribution of the particulate matter as well as suitable mixing of the air and exhaust. Tracer studies have shown that this mode of injection is far superior to introduction of the exhaust facing downstream or normal to the flow development tunnel 16. Studies have also shown that good mixing is achieved and that the sampling probes may be placed at almost any position within the flow development tunnel 16 and still produce a uniform result, as will be illustrated later. In order to assure thorough mixing of the exhaust and air the flow development tunnel 16 operates with a velocity of approximately 75 feet per second, although a range of 50 to 75 would be expected to be feasible. A residence time between the mixing of the cooled air stream and exhaust gases and the sampling of the mixture of about 0.1 seconds at this velocity has been found to be suitable for mixing, although a time between 0.1 and 0.15 seconds would be acceptable.

Tracer tests have also shown that the dimensions of the isokinetic sample probe 18 are critical to avoid deposition of particulate matter during the sampling, even though the probe is operated in an isokinetic manner. Deposition of these small particles is an exponential function of the surface to volume ratio of the probe itself and the length of the probe. Accordingly, the probe 18 must be kept as short as possible; a residence time within said isokinetic probe prior to the collecting of the particulates between 0.013 and 0.02 seconds being preferred. Although the inlet dimensions of the probe 18 are critical to isokinetic sampling, the probe 18 may be widened after the inlet in order to minimize the surface to volume ratio of the sample probe. However, lower velocities tend to create preferential deposition so this principle cannot be applied without consideration of such losses.

Figure 2:
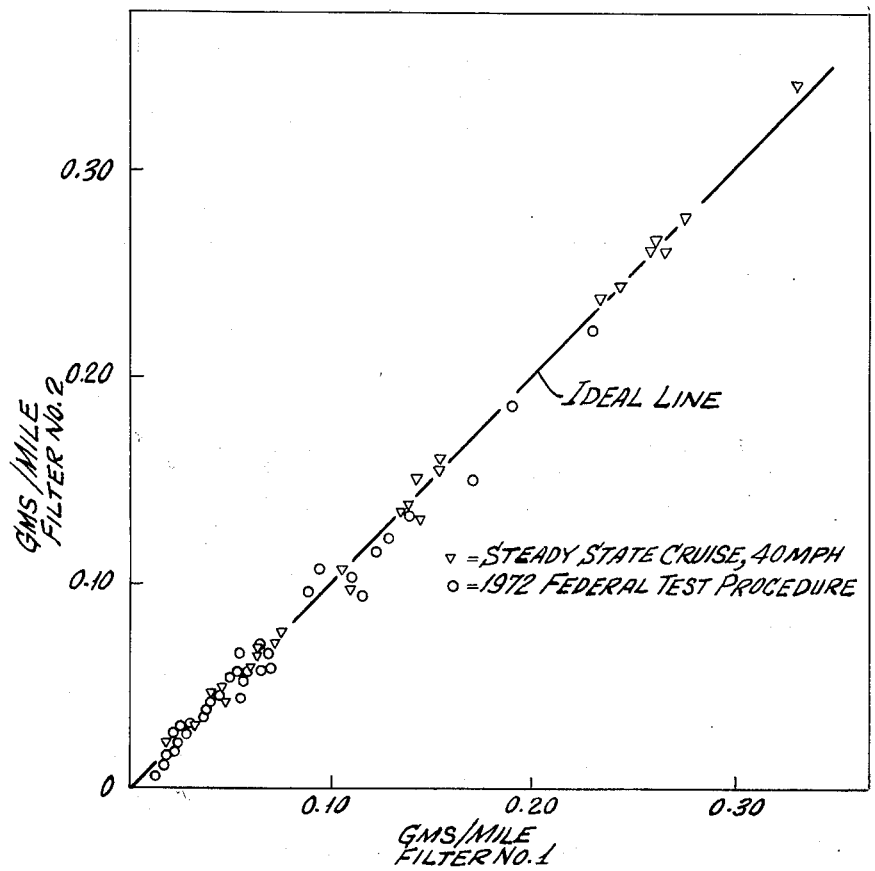
FIG. 2 illustrates the reproducibility of the results which are obtained by the method and apparatus of the invention.

Reproducibility of the sampling system is illustrated in FIG. 2 where results from a pair of probes are reproduced, illustrating that the results obtained from a probe located on one side of the tunnel 16 is essentially identical to that of a probe located on the opposite side of the duct. Such results were only possible when the proper design of the isokinetic sampling probe was undertaken. Initial results, even with isokinetic sampling, gave a wide disparity of results.

Figure 3:
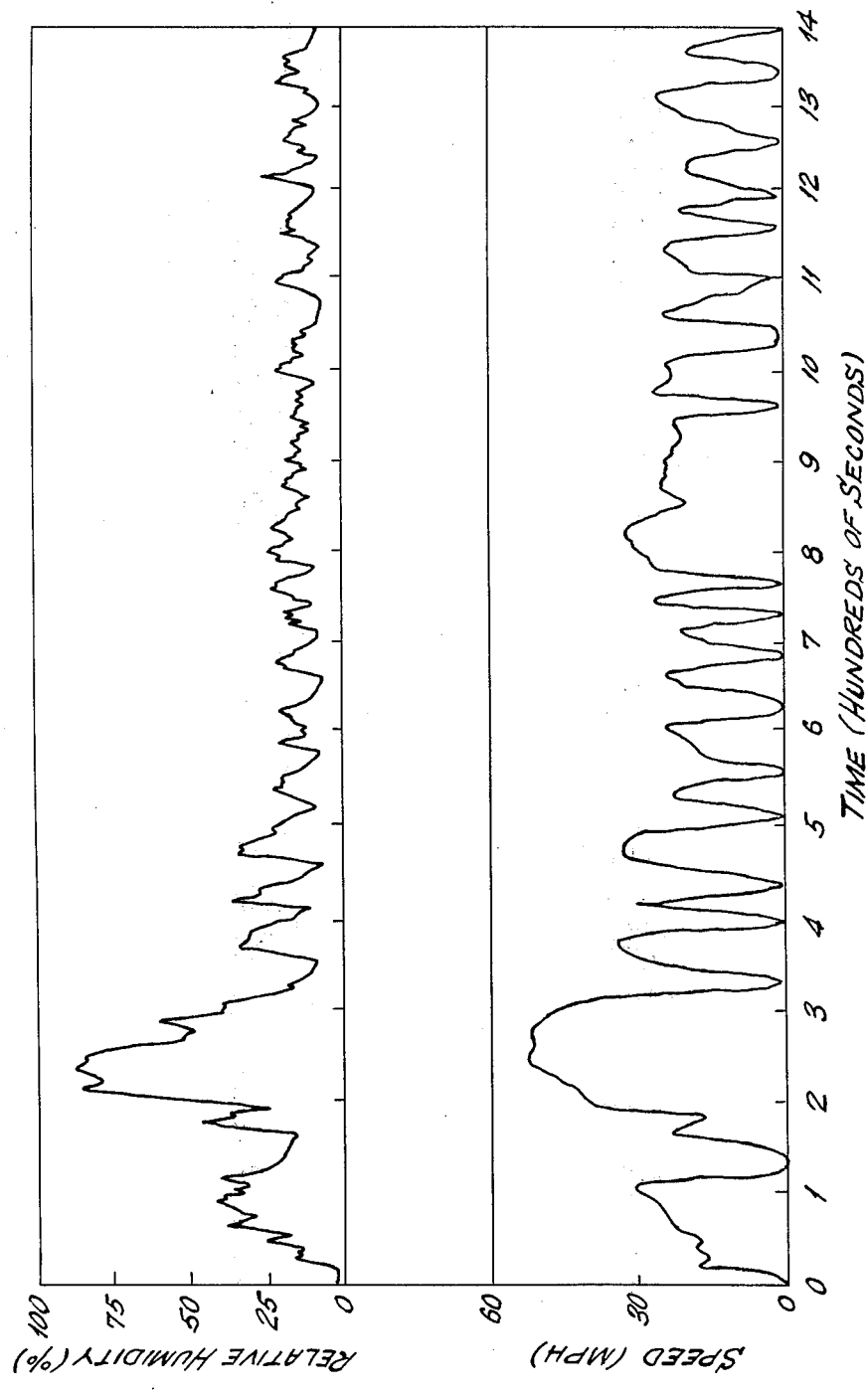
FIG. 3 illustrates the ability of the apparatus to prevent condensation in the apparatus during a typical test cycle.

FIG. 3 illustrates the relative humidity of the combined exhaust gas and air corresponding to various portions of the typical driving cycle. It will be noted that early in the cycle during rapid acceleration that relative humidity reaches its highest level, but still below the dew point, illustrating the ability of the system to control temperature and humidity so that condensation does not occur, even under the worst possible conditions. As previously noted, the figure below the relative humidity plot shows the speed variations of the vehicle during the standard 1972 EPA test cycle.

Figure 4:
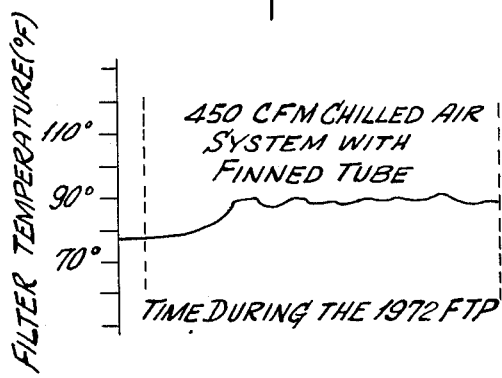
FIG. 4 illustrates the ability of the apparatus to control temperature at the filter during a typical test cycle with a vehicle having a catalytic exhaust system.
Figure 5:
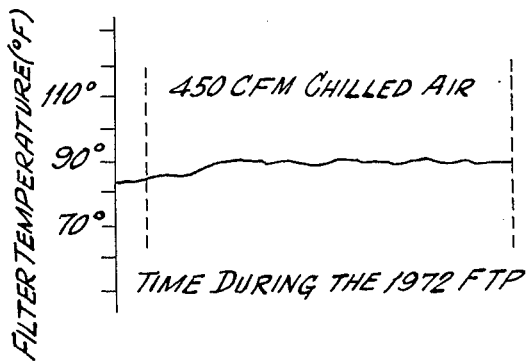
FIG. 5 illustrates the ability of the system to control temperature at the filter in measuring a typical vehicle without a catalytic exhaust system.

FIGS. 4 and 5 illustrate typical performance of the system, illustrating the ability to control temperature at the filter 20 during a typical test cycle. FIG. 4 illustrates results for a car equipped with a catalytic converter which inherently runs at a higher temperature exhaust than does that of the conventional vehicle without such a catalytic converter, illustrated by FIG. 5. In both cases it will be observed that the ability of the system to control temperature is quite satisfactory over the full cycle in spite of the sharp variations in vehicle operating conditions. The equipment, however, in its FIG. 1 configuration is not capable of controlling temperature when the exhaust temperature is quite low, as it is during the first minute or two of the driving cycle. No provision is made for heating the incoming air, which is required in order to achieve a 90°F. temperature at the filter 20. Under these conditions, however, condensation is no problem (see FIG. 3) and the filter is generally a more effective particle collector at lower temperatures, so that any particles which might be lost at 90°F. will probably be caught at temperatures below 90°F. It is believed, however, that this difference is insignificant to the results. Heating could be provided if desired only during this first few minutes.

The discussion of the preferred embodiment given herein is for information and illustration of the invention only and should not be considered to limit the scope thereof, which is defined by the claims which follow.

What is claimed is:
1. A method of collecting for measurement suspended particulates in exhaust gases from an internal combustion engine comprising:
   a. drying and filtering a stream of air to produce a diluent air stream;
   b. splitting said diluent air stream into a first portion and a second portion whose ratio is a function of the temperature at which said suspended particulates are collected;
   c. cooling said first portion of said diluent air stream and directing said second portion so as to bypass the cooling;
   d. mixing said cooled first portion of said diluent air stream and said second portion of said diluent air stream to provide a recombined diluent air stream;
   e. mixing said recombined diluent air stream with exhaust gases from an internal combustion engine such that the volume of said recombined diluent air stream plus the volume of exhaust gases is always equal to a constant volume;
   f. isokinetically extracting a sample from said constant volume of mixture of diluent air and exhaust gases with an isokinetic probe;
   g. passing said extracted sample through a filter and collecting said suspended particulates thereon at a substantially constant temperature; and
   h. measuring the temperature of said sample and controlling the amount of air in said first and second portions as a function of said measured temperature in order to maintain a constant temperature at said filter.

2. The method of claim 1 wherein said substantially constant temperature at said filter is maintained at substantially 90°F.

3. The method of claim 1 wherein the velocity of said recombined diluent air and exhaust gas is within the range of 50 to 75 feet per second.

4. The method of claim 3 wherein the residence time between the mixing of step (d) and the sampling of step (f) is between 0.10 and 0.15 seconds.

5. The method of claim 1 wherein the residence time within said isokinetic probe prior to the collecting of particulates in step (g) is within the range of 0.013 to 0.02 seconds.

6. The method of claim 1 wherein the drying of said air stream is sufficient to prevent condensation of water from the mixture of air and exhaust gas at the controlled temperature of said filter.

7. The method of claim 1 wherein the mixing of step (e) is accomplished by introducing the exhaust gas in an opposite direction to said stream of air.

8. An apparatus for collecting for measurement suspended particulates in the exhaust gases from internal combustion engines comprising:
 a. a filter for removing particulate matter from a stream of air;
 b. dessicant means for removing water vapor from said stream of air;
 c. means for splitting said stream of air which is filtered and dried into a first portion and a second portion, the ratio of which is in response to a predetermined temperature at which said suspended particulates are collected;
 d. cooling means for cooling said first portion of the dried and filtered stream of air;
 e. means for recombining said first and second portions of said stream of air after cooling said first portion, mixing means for combining said stream of air with exhaust gas containing particulates from an internal combustion engine, such that the volume of recombined first and second portion plus the volume of exhaust is maintained at a constant volume;
 f. an isokinetic sampling means for removing at a constant rate a sample of said constant volume of mixed air and exhaust gas;
 g. constant temperature filter means for collecting particulates sampled by said isokinetic sampling means;
 h. temperature measuring means for measuring the temperature of said mixed air and exhaust gas;
 i. temperature control means for maintaining the constant temperature in the filter means by adjusting the ratio of said first and second portion of said air stream;
 j. wherein the said means for splitting said air stream into first and second portions is resposnive to said temperature control means, thereby controlling the temperature of said recombined air stream of said first and second portions by adjusting the ratio of amount of air diverted around said cooling means and through said cooling means.

9. The apparatus of claim 8 wherein said filter of (a) has the capacity to remove essentially all particulates of 0.2 micron size and larger.

10. The apparatus of claim 8 wherein said desiccant mans has the capacity to remove sufficient water from said air to produce a dew point of at least 30°F.

11. The apparatus of claim 8 wherein said mixing means of (e) comprises an inlet nozzle for said exhaust gas directed into the flow of said air and a flow development tunnel fo completing the mixing.

12. The apparatus of claim 11 wherein said flow development tunnel is sized to provide a velocity in the range of 75 ft./sec. and a residence time of 0.1 second.

13. The apparatus of claim 8 wherein said isokinetic sampling means has a residence time between the inlet thereof and said filter of (g) of 0.013 seconds.

* * * * *